United States Patent
Macher et al.

(10) Patent No.: US 8,074,373 B2
(45) Date of Patent: Dec. 13, 2011

(54) ELECTRICALLY HEATABLE INSOLE

(75) Inventors: David Macher, Voitsberg (AT); Gerhard Schreiner, Graz (AT)

(73) Assignee: Therm-IC Products, Gleisdorf (AT)

( * ) Notice: Subject to any disclaimer, the term of this patent is extended or adjusted under 35 U.S.C. 154(b) by 863 days.

(21) Appl. No.: 10/588,174

(22) PCT Filed: Feb. 1, 2005

(86) PCT No.: PCT/EP2005/001100
§ 371 (c)(1),
(2), (4) Date: Jun. 5, 2008

(87) PCT Pub. No.: WO2005/072548
PCT Pub. Date: Aug. 11, 2005

(65) Prior Publication Data
US 2009/0013554 A1     Jan. 15, 2009

(30) Foreign Application Priority Data
Feb. 2, 2004   (DE) .................. 10 2004 006 046

(51) Int. Cl.
*A43B 7/04*    (2006.01)
*H05B 3/00*    (2006.01)
(52) U.S. Cl. .................. 36/2.6; 36/43; 219/211
(58) Field of Classification Search ............ 36/2.6, 36/137, 43, 44, 71; 219/211, 523, 528
See application file for complete search history.

(56) References Cited

U.S. PATENT DOCUMENTS

| | | | |
|---|---|---|---|
| 4,080,971 A * | 3/1978 | Leeper | 607/111 |
| 4,910,881 A * | 3/1990 | Baggio et al. | 36/2.6 |
| 5,495,682 A | 3/1996 | Chen | |
| 5,667,290 A * | 9/1997 | Cioletti et al. | 362/473 |
| 5,956,866 A * | 9/1999 | Spears | 36/2.6 |
| 6,657,164 B1 | 12/2003 | Koch | |
| 2002/0133973 A1* | 9/2002 | Lin | 36/2.6 |
| 2004/0164066 A1* | 8/2004 | Ford et al. | 219/211 |

FOREIGN PATENT DOCUMENTS

| | | |
|---|---|---|
| DE | 3904603 | 8/1990 |
| DE | 4000259 | 7/1991 |
| DE | 19538204 | 4/1997 |
| DE | 29817506 | 2/1999 |
| DE | 29817003 | 5/1999 |
| DE | 29821470 | 6/1999 |
| DE | 20317143 | 5/2004 |
| EP | 0162031 | 11/1985 |
| WO | 95/01740 | 1/1995 |
| WO | 02/49472 | 6/2002 |

* cited by examiner

*Primary Examiner* — Jila Mohandesi
(74) *Attorney, Agent, or Firm* — Fay Kaplun & Marcin, LLP

(57) ABSTRACT

An electrically heatable in sole may include at least one sole base body and one covering layer, at least one heating electrode, at least one rechargeable battery that is electrically connected to the heating electrode, and a control circuit for controlling the heating process and the charging of the battery. Heating electrodes, rechargeable batteries and a control circuit are arranged in the base body of the sole and/or between the base body and the covering layer. The control circuit includes a remote control device for starting and stopping the heating process, and a protection circuit for disconnecting the rechargeable batteries in the event of an error.

15 Claims, 2 Drawing Sheets

ELECTRICALLY HEATABLE INSOLE

FIELD OF INVENTION

The present invention relates to an electrically heatable.

BACKGROUND INFORMATION

A heatable shoe sole is known from DE 39 04 603 A1 which is constructed from a plurality of layers, one layer which serves for generating heat being formed from a conductive plastic material foil with strip conductors deposited thereon. In the central foot region of the sole, a cold conductor switch element is provided on the underside of the heating foil, said switch element registering the actual temperature present and switching on the heating at a predetermined temperature and, upon reaching a further predetermined temperature, switching it off again. In the region of the heel, a rechargeable battery with an inductive charging coil and rectifier is provided.

SUMMARY OF INVENTION

The present invention relates to an electrically heatable insole which provides flexible usage options and is simple to operate.

As a result of the fact that the control circuit disposed in the sole has a remote control device for switching on and off or controlling the heating process, the heating process can be used by the user in a flexible manner independently of the temperature attained and can be switched off and on simply according to his wishes. By providing a protective circuit for disconnecting the rechargeable battery from the remaining current circuit, too great a heat development is prevented from taking place in the case of a short circuit or the like, which can be dangerous for the user.

In particular, the heating electrode can be actuated by pulsating voltage. The frequency of these impulses is tuned such that in addition the blood circulation is stimulated. Since normal batteries lose power at low temperatures, this type of heating process has a second advantage: the batteries are under load for a short time. Subsequently, they are given a short regeneration phase in which they can recover. This increases the power capacity to a large degree at low temperatures and also extends the lifespan of these cells.

Due to the measures indicated in the subclaims, advantageous developments and improvements are possible.

It is particularly advantageous that the rechargeable battery is a lithium accumulator since the accumulators are especially flat and withstand the loading by the heel pressure. Preferably, LI ions or LI polymer accumulators can be used since they deliver the necessary power in the case of a smaller, above all flat construction.

The choice of batteries used is of particular importance: on the one hand, these must have a correspondingly high capacity in order to achieve acceptable heating times and temperatures, on the other hand, they must be small and light in order not to restrict the comfort when moving. This demands a high energy density, such as cannot be achieved for example with conventional nickel accumulators.

Rechargeable lithium-ion cells have a suitable high energy density. Because of the high energy density, such batteries represent a risk potential however. A short circuit would lead to an explosion of the cells. Furthermore the cells must also be protected from excess currents and total discharge, both events which lead to total destruction of the cells. Only the feature according to the invention of a protective circuit allows sensible use of such cells in a sole.

Lithium, which already has an extreme reaction chemically with normal atmospheric humidity, must also be protected against mechanical damage (stepping on a nail). Mechanical protection is ensured by a metal cage which surrounds the battery.

Alternatively, also lithium-ion polymers can be used as batteries. Because of their flexibility, these are particularly suitable for use in a sole. Since dry batteries are of concern here, there is no danger of an explosion in the case of a short circuit or mechanical damage (stepping on a nail). However, a protective circuit is also sensible here since even this type of battery must be protected from overloading or excess currents and total discharge in order to prevent total destruction of the battery.

Because of its properties, use of lithium-ion polymers would be preferred over the use of the above-described wet cells. It is however disadvantageous that lithium-ion polymers are very expensive.

Preferably, the rechargeable battery or the rechargeable batteries is or are disposed in the heel region and/or in the foot arch region of the insole.

The region between the arch of the foot and the toes remains preferably unoccupied. This is particularly advantageous for the rolling movement when walking/running. In this respect, in particular the use of flexible lithium accumulators should be stressed: the wearing comfort of the insole is considerably improved by the flexibility. As a more inexpensive variant, also standard batteries can be used, around which a rigid housing is positively placed for protection.

Preferably, the heating electrode has Minimelf resistors.

Minimelfs are electrical miniature resistors with a cylindrical construction, approx. 3 mm long and with a diameter of approx. 1 mm. These resistors are disposed in the sole along bending lines which are present.

The cylindrical construction and the special arrangement is crucial here. If prismatic SMD resistors were used here, these would immediately break through the rectangular support surface when subjected to bending of the board.

These resistors are connected via strip conductors. The strip conductors have a planar configuration in order to achieve good heat dispersion from the heating electrode to the foot. Furthermore, the heating electrode is embedded in a body made of plastic material or disposed on said body. As a result, the required stability is achieved.

Preferably, the control circuit is a control circuit for continuous regulation of the strength of the heating process.

With one adjustment switch, one is restricted to a small number of fixed adjustments of the strength of the heating process, the temperature can only be altered within rough steps. According to the invention, electronic components and software are however provided in the control circuit. As a result, the size of the steps can be adjusted in a considerably finer manner relative to an adjustment switch. The resolution is adjustable such that a wearer of the sole can (almost) no longer detect the temperature difference between adjacent temperature steps. Hence the impression of continuous regulation is conveyed.

Preferably, the remote control device has an external operating part with an actuation element, e.g. a push-button or switch, via which an on or off signal is issued to a control part of the remote control device incorporated in the sole by means of a transmitter, e.g. an IR transmitter or an ultrasonic transmitter, said signal in turn activating or deactivating the heating.

In an advantageous manner, the remote control device can also have a contact-free switch, a switch element being disposed in the operating part and a second switch element in the control part.

In an advantageous manner, the operating part (10) can have a receiver and the remote control device can be a bi-directional remote control.

It must hence be taken into account with a remote control that the signal transmission is partially subject to interference. The object underlying this development is hence to ensure that the operating state of the respective sole corresponds to the settings of the operating part or to the display on the operating part. In other words: defects in the signal transmission are intended to have no effect as far as possible.

The control according to the invention achieves this object in the following manner: the remote control device and the operating part are both equipped with transmitting and receiving units. The remote control device of the respective sole can communicate with the operating part. Via the operating part, the wearer of the sole sets the desired parameter, for example the heat output. This is conveyed from the operating part to the remote control device of the respective sole.

In order to ensure that the signals of the operating part have reached the sole, i.e. that for example the heat output chosen on the operating part is actually set also by the sole, an acknowledgement of the transmitting signal is provided: the remote control device of the respective sole confirms having obtained the signal from the operating part. If the operating part receives the acknowledgement from both soles, then it is ensured that the selected heat output is present in both soles.

Further parameters which can be correctly conveyed in this way, are accumulator voltage, temperature of the respective sole and the state of the heating electrode or the heating element, to mention a few examples.

The functional capability of the operating part can also be monitored with a bi-directional remote control: if the remote control fails for example, then the remote control device detects this by the fact that transmitted signals are no longer acknowledged. A corresponding reaction can follow thereafter, such as for example lowering of the heat output.

Furthermore, identification of the respective receiving and transmitting units is provided. It is hence ensured that in the case where a plurality of systems is located in a narrow space, no mutual interference of these systems occurs.

It is particularly advantageous that a plug contact is incorporated in the sole base body, to which a network device for recharging the accumulators can be connected. However a contact-free recharging of the accumulators, e.g. by induction, can also be effected.

BRIEF DESCRIPTION OF DRAWINGS

An embodiment of the present invention is represented in the drawing and is explained in more detail in the subsequent description. There are shown.

DETAILED DESCRIPTION

Figure 1:
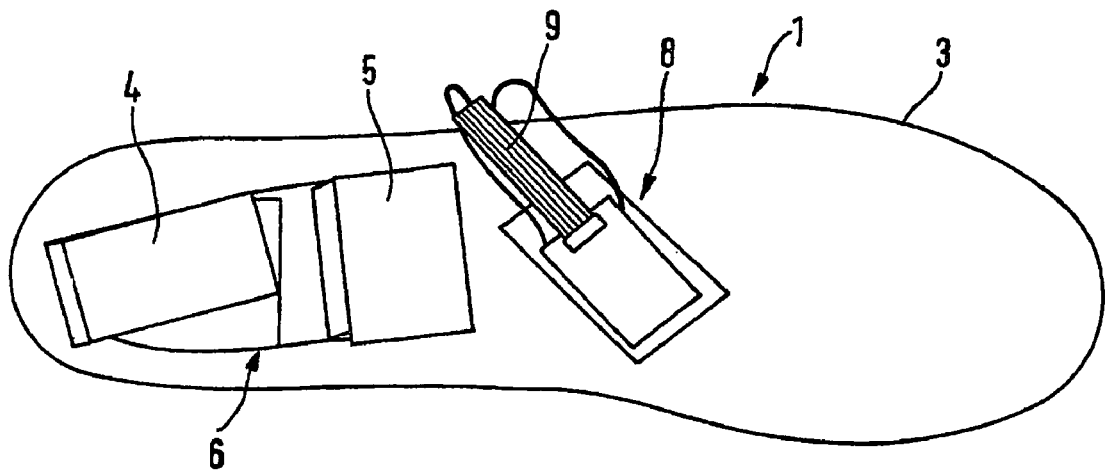
FIG. 1 shows an exemplary embodiment of an insole according to the present invention, parts of the cover layer being cut out.
Figure 3:
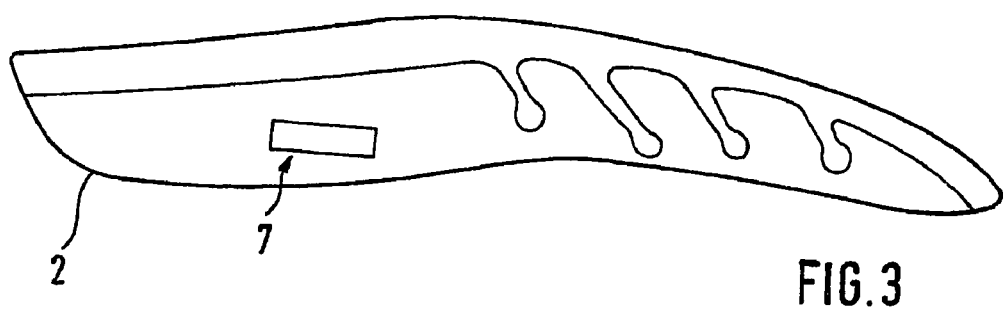
FIG. 3 shows a side view on the rear part of an insole.

The insole illustrated in FIG. 1 and FIG. 3 comprises a sole basic body 2 which corresponds for example to an orthopaedic sports insert and can comprise a moulded body or a plurality of layers, and a cover layer 3 which is orientated towards the foot of the user.

Electronic components are embedded in the sole basic body 2, recesses for two lithium accumulators 4, 5 being provided in the heel region, which can be configured as LI-ion or LI-polymer accumulator cells. Furthermore a preferably encapsulated protective and charging circuit 6 is inserted in the basic body 2, the protective circuit separating the accumulators from the remaining circuit in the case of a large heat development. The heating electrodes which are disposed in particular in the front foot region under the cover layer 3 over a large area and which comprise resistor faces cannot be seen in the Figure. The heating electrodes are connected to the accumulators 4, 5 via the protective circuit 6. The protective circuit has temperature and current sensors and an intelligent logic which takes over control or disconnection of the heating electrodes. In addition, the lithium accumulators are incorporated in a protective housing in order that the user does not suffer harm in the case of an explosion of the battery. In this case, the pressure wave is absorbed and the heat in the shoe is dispersed downwardly.

In the illustrated embodiment, the charging circuit 6 is connected to a plug contact 7 which is likewise incorporated in the sole basic body 2 and uncovers its plug elements outwardly. A network device for charging can be connected to this plug contact.

Furthermore, a remote control 8 in the form of a fitted printed circuit board is inserted in the basic body 2, said printed circuit board being connected to the protective and charging circuit 6 and to the heating electrodes, not shown, and which controls the connection and disconnection of the heating electrodes. The connection lines 9 are shown here above the cover layer 3. Of course, they are likewise inserted underneath the cover layer in the sole basic body. The remote control normally has a transmitting and receiving mechanism which operates with infrared rays or ultrasound or other modulated radio signals. The frequency ranges can be in the long-wave, microwave, HF or UHF range.

Furthermore, electronic switch elements are provided which control the voltage supply between accumulators 4, 5 and heating elements. In addition, temperature sensors can be provided which serve likewise for controlling the heating elements.

Figure 2:
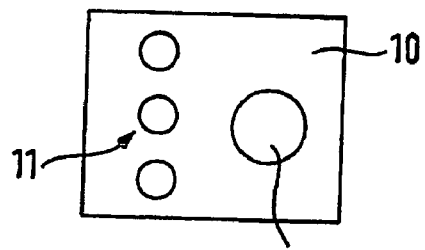
FIG. 2 shows a schematic view on the operating part of the remote control.

The operating part 10 for the remote control, which can be configured for example as a key-ring attachment or the like and is illustrated schematically in FIG. 2, likewise has a transmitting and receiving device which provides signals to the remote control part 8 in the sole and receives them from the latter. Furthermore, a plurality of display elements 11 is provided which can be configured as LEDs and which display the switching state and/or temperatures. Furthermore, the operating part 10 has a push-button or push-switch 12 which generates a switch-on or switch-off signal or selection signals for the temperature steps, which is transmitted via the transmitting and receiving mechanism to the remote control part 8 in the sole 1.

Furthermore, the control circuit is configured as a "continuous" control. The necessary electronics and software are integrated in the control circuit. The wearer can adjust the temperature which is most pleasant for him via the operating part 10. The adjustment is actuated via the push-button 12.

The control circuit is a control circuit for a pulsating heating process, i.e. heating impulses are emitted at a frequency coordinated to the blood circulation. Alternatively a constant heating process can also be provided.

The remote control of this system of sole-operating part has a bi-directional configuration. The respective received signals are acknowledged via a response signal. It is hence ensured that the receiver has obtained the signal, that for example the temperature selected at the operating part 10 was actually transmitted to the remote control device in the soles.

Figure 4:
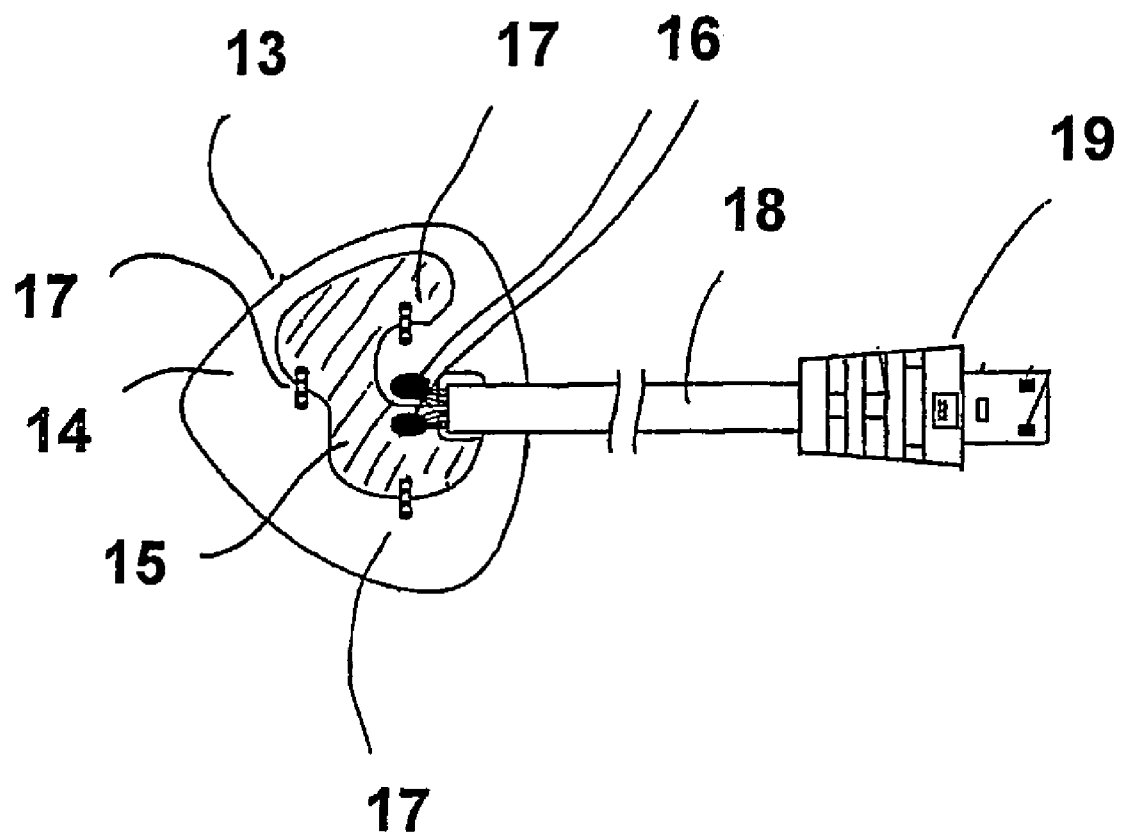
FIG. 4 shows a schematic view on a heating electrode.

FIG. 4 shows a schematic view of a heating electrode according to the invention.

A board 13 is shown. The board is embedded in the front region in the sole. It covers this front region over a large area. The board comprises epoxy resin and is flexible. As a result the flexibility of the sole is also maintained. Alternatively, other flexible plastic materials or plastic material resins can however also be used.

The board is almost entirely coated with copper. This copper layer is thereby separated galvanically into a first region 14 and into a second region 15. These two regions are contacted with two electrodes 16. Via cable 18 and a plug 19, the electrodes 16 are connected to the control circuit, not shown in this Figure.

The electrical connection between the first region 14 and the second region 15 is produced via three cylindrical Minimelf resistors 17 with a resistance of 27 ohm and connected in parallel. These resistors are soldered directly onto the copper layer. They are orientated in the longitudinal direction according to the bending lines of the sole.

The resistors are disposed on the board in such a manner that they cover respectively as large a region as possible of the board which does not overlap with the region of another resistor.

Alternatively, a different number of resistors can also be used. This is dependent inter alia upon the size of the surface which is to be heated.

If a voltage is now applied to the electrodes 16, then the resistors 17 are heated. Since these resistors are soldered directly on the regions 14 and 15 of the copper layer, these resistors emit their heat directly to the copper layer. Due to the arrangement of the resistors, large heat distributions or temperature gradients on the copper layer are prevented. The copper layer distributes the heat rapidly and over a large area.

In another embodiment, a contact-free switch can be used for switching on and switching off, which is configured for example as a magnetic switch, proximity switch or the like and in which a first switching element is provided instead of the push-button 12 in the operating part 10 and a second switching element is disposed in the so-called "remote control" in the sole. In this case, a transmitter can likewise be provided in the sole and a receiver in the operating part 10 in order to transmit information about the starting state and if necessary temperatures to the display elements 11.

In yet another embodiment, these display elements can be omitted and the operating part 10 comprises merely the first switching element.

The invention claimed is:

1. An electrically heatable insole, comprising:
   at least one sole basic body;
   a cover layer;
   at least one heating electrode;
   at least one rechargeable battery electrically connected to the heating electrode; and
   a control circuit controlling a heating process and recharging the battery,
   wherein the heating electrode, the battery and the control circuit are disposed at least one of (i) in the sole basic body and (ii) between the sole basic body and the cover layer,
   wherein the control circuit includes (i) a remote control device switching the heating process on and off and (ii) a protective circuit disconnecting the battery in an event of a defect, and
   wherein the remote control comprises a control part incorporated in the sole.

2. The insole according to claim 1, wherein the battery is a lithium accumulator.

3. The insole according to claim 1, wherein the battery is disposed in at least one of (i) a heel region and (ii) a foot arch region of the insole.

4. The insole according to claim 1, wherein the heating electrode includes Minimelf resistors.

5. The insole according to claim 1, wherein the control circuit continuously regulates a strength of the heating process.

6. The insole according to claim 1, wherein the remote control device has an external operating part.

7. The insole according to claim 1, wherein the remote control device has a contact-free switch.

8. The insole according to claim 1, wherein the remote control device has a transmitting and receiving unit which wirelessly transmits information.

9. The insole according to claim 6, wherein the operating part includes display elements for at least one of (i) a functional display and (ii) a temperature display.

10. The insole according to claim 6, wherein the operating part has a transmitter and an actuation element which activates the transmitter, the transmitter, in an activated state, transmitting a wireless switch-on signal to the incorporated control part.

11. The insole according to claim 8, wherein the operating part has a receiver and the remote control device is a bi-directional remote control.

12. The insole according to claim 6, wherein the operating part includes a first switching element of a contact-free switch which cooperates with a second switching element disposed in the incorporated control part.

13. The insole according to claim 7, wherein the contact-free switch is configured as one of a reed switch, a magnetic switch and a proximity switch.

14. The insole according to claim 1, wherein a plug contact connected to the control circuit for connection of a network device is incorporated in the sole basic body.

15. An electrically heatable insole, comprising:
   at least one sole basic body;
   a cover layer;
   at least one heating electrode;
   at least one rechargeable battery electrically connected to the heating electrode; and
   a control circuit controlling a heating process and recharging the battery,
   wherein the heating electrode, the battery and the control circuit are disposed at least one of (i) in the sole basic body and (ii) between the sole basic body and the cover layer,
   wherein the control circuit includes (i) a remote control device switching the heating process on and off and (ii) a protective circuit disconnecting the battery in an event of a defect, and
   wherein the remote control device has a transmitting and receiving unit which wirelessly transmits information.

* * * * *